US011490927B2

(12) United States Patent
Evans et al.

(10) Patent No.: US 11,490,927 B2
(45) Date of Patent: Nov. 8, 2022

(54) POWERED SURGICAL DEVICE WITH SPEED AND CURRENT DERIVATIVE MOTOR SHUT OFF

(71) Applicant: Covidien LP, Mansfield, MA (US)

(72) Inventors: Christopher Kelly Evans, Southington, CT (US); Anthony Calderoni, Bristol, CT (US)

(73) Assignee: Covidien LP, Mansfield, MA (US)

(*) Notice: Subject to any disclaimer, the term of this patent is extended or adjusted under 35 U.S.C. 154(b) by 689 days.

(21) Appl. No.: 16/549,595

(22) Filed: Aug. 23, 2019

(65) Prior Publication Data
US 2019/0374253 A1  Dec. 12, 2019

Related U.S. Application Data

(63) Continuation of application No. 15/946,327, filed on Apr. 5, 2018, now Pat. No. 10,390,858.
(Continued)

(51) Int. Cl.
| H02P 7/00 | (2016.01) |
| A61B 17/34 | (2006.01) |
| A61B 17/072 | (2006.01) |
| A61B 17/00 | (2006.01) |
| A61B 17/32 | (2006.01) |
| A61B 90/00 | (2016.01) |

(52) U.S. Cl.
CPC .... *A61B 17/3476* (2013.01); *A61B 17/00234* (2013.01); *A61B 17/072* (2013.01); *A61B 17/07207* (2013.01); *A61B 17/320016* (2013.01); *A61B 90/03* (2016.02); *A61B 2017/00017* (2013.01); *A61B 2017/00039* (2013.01); *A61B 2017/0046* (2013.01); *A61B 2017/00075* (2013.01); *A61B 2017/00123* (2013.01); *A61B 2017/00389* (2013.01); *A61B 2017/00398* (2013.01); *A61B 2017/00464* (2013.01); *A61B 2017/00477* (2013.01); *A61B 2017/00725* (2013.01); *A61B 2017/00734* (2013.01)

(58) Field of Classification Search
CPC .................................................. A61B 17/3476
USPC ......................................................... 318/432
See application file for complete search history.

(56) References Cited

U.S. PATENT DOCUMENTS

| 2,777,340 A | 1/1957 | Hettwer et al. |
| 2,957,353 A | 10/1960 | Babacz |
(Continued)

FOREIGN PATENT DOCUMENTS

| CA | 2451558 A1 | 1/2003 |
| CN | 1547454 A | 11/2004 |
(Continued)

OTHER PUBLICATIONS

Japanese Office Action dated Feb. 14, 2022 issued in corresponding JP Appln. No. 2018-086076.
(Continued)

*Primary Examiner* — Erick D Glass
(74) *Attorney, Agent, or Firm* — Carter, DeLuca & Farrell LLP

(57) ABSTRACT

A surgical instrument includes: an end effector; a power source; a motor coupled to the power source, the motor configured to actuate the end effector; and a controller operatively coupled to the motor and configured to control the motor based on a current draw of the motor and an angular velocity of the motor.

15 Claims, 7 Drawing Sheets

Related U.S. Application Data

(60) Provisional application No. 62/500,236, filed on May 2, 2017.

(56) References Cited

U.S. PATENT DOCUMENTS

| | | | |
|---|---|---|---|
| 3,111,328 A | 11/1963 | Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |

(56) References Cited

U.S. PATENT DOCUMENTS

| | | |
|---|---|---|
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 3,052,024 A1 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |

(56) References Cited

U.S. PATENT DOCUMENTS

| | | |
|---|---|---|
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2016/0256153 A1 | 9/2016 | Shelton, IV et al. |
| 2016/0310134 A1 | 10/2016 | Contini et al. |

FOREIGN PATENT DOCUMENTS

| | | |
|---|---|---|
| CN | 1957854 A | 5/2007 |
| CN | 101495046 A | 7/2009 |
| CN | 101532361 A | 9/2009 |
| CN | 102247182 A | 11/2011 |
| DE | 102008053842 A1 | 5/2010 |
| EP | 0705571 A1 | 4/1996 |
| EP | 1563793 A1 | 8/2005 |

(56) References Cited

FOREIGN PATENT DOCUMENTS

| | | |
|---|---|---|
| EP | 1769754 A1 | 4/2007 |
| EP | 2316345 A1 | 5/2011 |
| EP | 2668910 A2 | 12/2013 |
| EP | 2684529 A2 | 1/2014 |
| EP | 2724674 A2 | 4/2014 |
| EP | 2789299 A1 | 10/2014 |
| ES | 2333509 A1 | 2/2010 |
| JP | 2005125075 A | 5/2005 |
| JP | 2011189128 | 9/2011 |
| JP | 2014083440 A | 5/2014 |
| KR | 20120022521 A | 3/2012 |
| WO | 2011108840 A2 | 9/2011 |
| WO | 2012/040984 A1 | 4/2012 |
| WO | 2012040984 A1 | 4/2012 |
| WO | 2017053698 A1 | 3/2017 |

OTHER PUBLICATIONS

European Examination Report dated Nov. 8, 2019 issued in corresponding EP Appln. No. 18170246.5.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.
Extended European Search Report dated Jan. 3, 2019 issued in corresponding EP Appln. No. 18170246.5.
Extended European Search Report corresponding to International Application No. EP 14 18 4882.0 dated May 12, 2015.
Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Chinese Office Action dated Jul. 5, 2022 issued in corresponding CN Appln. No. 201810400108.8.

POWERED SURGICAL DEVICE WITH SPEED AND CURRENT DERIVATIVE MOTOR SHUT OFF

CROSS-REFERENCE TO RELATED APPLICATIONS

This application is a continuation of U.S. patent application Ser. No. 15/946,327, filed on Apr. 5, 2018, which claims the benefit of and priority to U.S. Provisional Patent Application No. 62/500,236 filed May 2, 2017. The entire disclosures of all of the foregoing applications are incorporated by reference herein.

BACKGROUND

1. Technical Field

The present disclosure relates to surgical devices. More specifically, the present disclosure relates to handheld electromechanical surgical systems for performing surgical procedures having reusable components.

2. Background of the Related Art

Linear clamping, cutting and stapling devices are used in surgical procedures to resect cancerous or anomalous tissue from a gastro-intestinal tract. Conventional linear clamping, cutting and stapling instruments include a pistol grip-styled structure having an elongated shaft and an end effector having a pair of gripping members disposed at a distal end of the shaft to clamp, cut, and staple tissue. Actuation of the gripping members is usually accomplished by actuating a trigger coupled to the handle, in response to which one of the two gripping members, such as the anvil portion, moves or pivots relative to the elongated shaft while the other gripping element remains fixed. The fixed gripping member includes a staple cartridge and a mechanism for ejecting the staples through the clamped tissue against the anvil portion, thereby stapling the tissue. The end effector may be integrally formed with the shaft or may be detachable allowing for interchangeability of various gripping and stapling members.

A number of surgical device manufacturers have also developed proprietary powered drive systems for operating and/or manipulating the end effectors. The powered drive systems may include a powered handle assembly, which may be reusable, and a disposable end effector that is removably connected to the powered handle assembly.

Many of the existing end effectors for use with existing powered surgical devices and/or handle assemblies are driven by a linear driving force. For example, end effectors for performing endo-gastrointestinal anastomosis procedures, end-to-end anastomosis procedures, and transverse anastomosis procedures, are actuated by a linear driving force. As such, these end effectors are not compatible with surgical devices and/or handle assemblies that use rotary motion.

Many of these electromechanical surgical devices include complex drive components. To prevent actuation of drive mechanisms beyond mechanical limits, various switches and sensors are used to detect operational state of the surgical devices. Inclusion of multiple switches and/or sensors adds to the cost and complexity of the surgical devices. Accordingly, there is a need for systems and apparatuses having safety mechanisms that can detect mechanical limits without relying on multiple mechanical limit sensors and/or switches disposed throughout the surgical device.

SUMMARY

According to one embodiment of the present disclosure, a surgical instrument is provided. The surgical instrument includes: an end effector; a power source; a motor coupled to the power source, the motor configured to actuate the end effector; and a controller operatively coupled to the motor and configured to control the motor based on a current draw of the motor and an angular velocity of the motor.

According to one aspect of the above embodiment, the surgical instrument further includes a motor control circuit configured to measure the current draw of the motor and the angular velocity of the motor.

According to another aspect of the above embodiment, the controller may be configured to calculate an instantaneous rate of change of each of the current draw of the motor and the angular velocity of the motor.

According to a further aspect of the above embodiment, the controller may be further configured to determine that the motor reached a mechanical limit based on the instantaneous rate of change of the current draw of the motor being positive and the instantaneous rate of change of the angular velocity of the motor being negative. The controller may also be configured to determine that the motor reached a mechanical limit based on the instantaneous rate of change of the current draw of the motor exceeding a first threshold, concurrently or otherwise, with the instantaneous rate of change of the angular velocity of the motor exceeding a second threshold.

According to one aspect of the above embodiment, the controller is configured to calibrate the motor based on the mechanical limit. The controller may also be configured to terminate the supply of electrical current to the motor from the power supply in response to detection of the mechanical limit.

According to another embodiment of the present disclosure, a method for controlling a surgical device is provided. The method includes: energizing a motor to actuate an end effector; measuring a current draw of the motor; measuring an angular velocity of the motor; and controlling the motor based on the current draw of the motor and the angular velocity of the motor.

According to one aspect of the above embodiment, the method includes calibrating the motor based on the mechanical limit.

According to another aspect of the above embodiment, the method further includes terminating a supply of electrical current to the motor from the power supply in response to detection of the mechanical limit.

According to a further embodiment of the present disclosure, a method for calibrating a surgical instrument is disclosed. The method includes: energizing a motor to actuate an end effector; measuring a current draw of the motor; measuring an angular velocity of the motor; detecting the motor reaching a mechanical limit based on the current draw of the motor and the angular velocity of the motor; and designating an angular position of the motor corresponding to the mechanical limit as a zero position for calibrating the motor.

According to one aspect of any of the above method embodiments, the methods may include calculating an instantaneous rate of change of each of the current draw of the motor and the angular velocity of the motor. The methods may also include determining that the motor reached the mechanical limit based on the instantaneous rate of change of the current draw of the motor being positive and the instantaneous rate of change of the angular velocity of the motor being negative.

According to another aspect of any of the above embodiments, the methods may include determining that the motor reached the mechanical limit based on the instantaneous rate of change of the current draw of the motor exceeding a first threshold, concurrently or otherwise, with the instantaneous rate of change of the angular velocity of the motor exceeding a second threshold.

DESCRIPTION OF THE DRAWINGS

Embodiments of the present disclosure are described herein with reference to the accompanying drawings, wherein.

DETAILED DESCRIPTION

Figure 1:
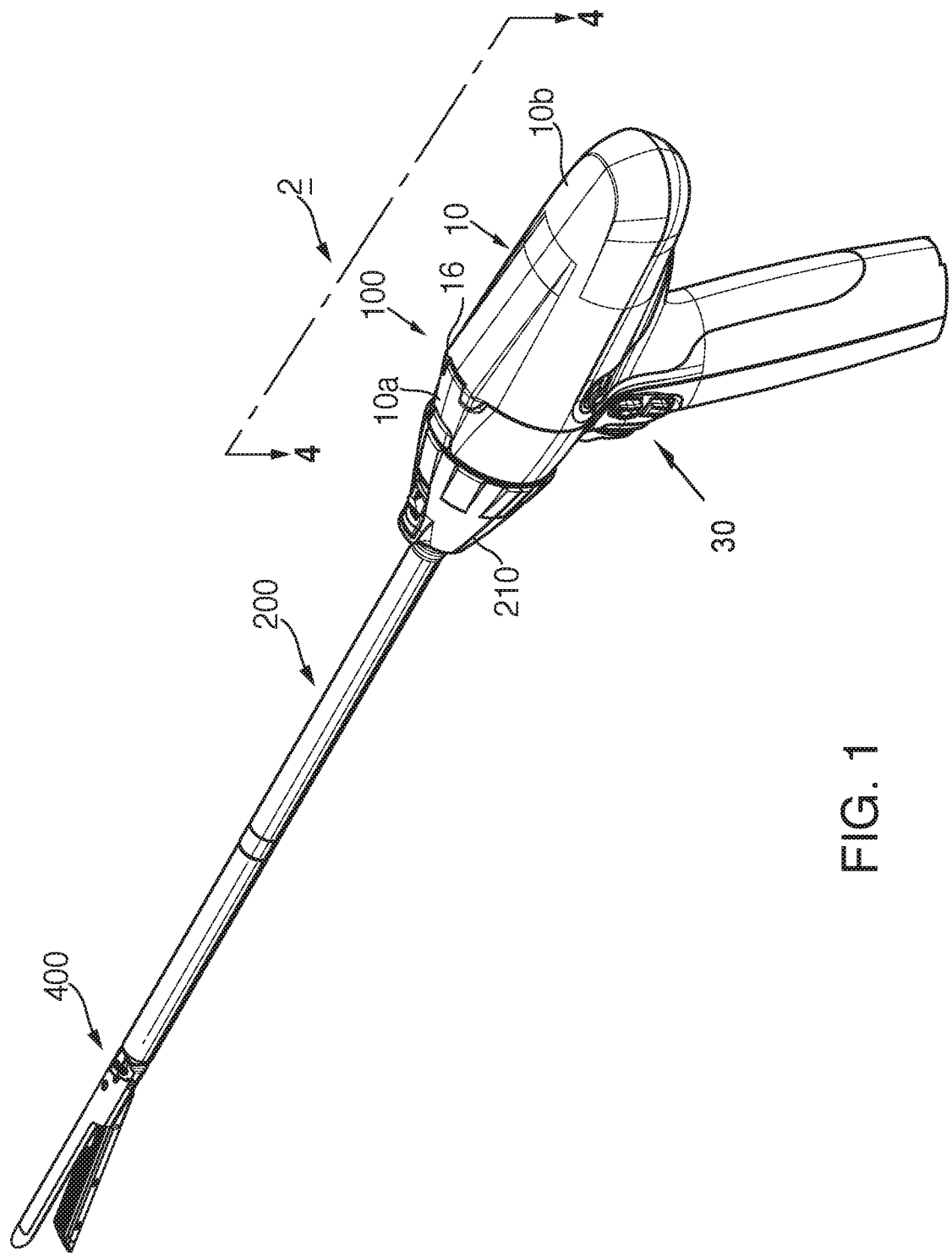
FIG. 1 is a perspective view of a surgical system including a handheld surgical device, an adapter assembly, and an end effector according to an embodiment of the present disclosure.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

The present disclosure provides a powered surgical device including one or more motors configured to actuate a surgical end effector and one or more sensors configured to monitor motor operation, such as current draw and angular velocity. The powered surgical device also includes a controller coupled to, and configured to control the motor based on feedback from the sensors. The controller is configured to shut off the motor in the event of a collision, which is determined based on a rate of change of angular velocity and current draw by the motor. The angular velocity and current draw may be plotted as a function of time and the slope of each plot may then be calculated using a derivative function to determine the rate of change of each of the angular velocity and the motor current. These two outputs of the motor movement may be tracked simultaneously. In the event of a collision, motor speed is reduced, thereby creating a negative slope, or rate of change, and motor current increases with the increasing load causing a positive slope, or rate of change. Once a negative motor speed derivative and a positive current derivative simultaneously exceed respective preset thresholds, the controller shuts down the motor. In embodiments, the sensitivity of the surgical device may be tuned by varying the derivative thresholds to eliminate false detections and prevent damage to the driven mechanisms.

The system and method according to the present disclosure allows for detection of an imminent collision prior (e.g., by about 40 milliseconds) to mechanical components of the surgical device actually encountering the mechanical limit. Early detection allows for the controller to decrease or shut down the motor thereby reducing the force applied to the mechanical components of the surgical device. This would prevent damage to mechanical components as well as conserve power and reduce stress on a power supply of the surgical device, (e.g., a battery) since current draw during the collision is reduced. In embodiments, collision detection of the present disclosure may also be utilized in intentional collisions, e.g., attempts to reach mechanical limits, to calibrate the motor.

As illustrated in FIG. 1, a surgical system 2 according to the present disclosure includes a surgical device 100, which is shown as a powered hand held electromechanical instrument, configured for selective attachment to a plurality of different end effectors or single use loading units ("SU-LU's"), such as an end effector 400. In particular, surgical device 100 is configured for selective connection with an adapter 200, and, in turn, adapter 200 is configured for selective connection with the end effector 400.

With reference to FIGS. 1-4, surgical device 100 includes a power-pack 101 (FIG. 2), and an outer shell housing 10 configured to selectively receive and enclose the power-pack 101. Outer shell housing 10 includes a distal half-section 10a and a proximal half-section 10b. The proximal half-section 10b pivotably connected to distal half-section 10a by a hinge 16 located along an upper edge of distal half-section 10a and proximal half-section 10b such that distal and proximal half-sections 10a, 10b are divided along a plane that traverses a longitudinal axis defined by adapter 200. When joined, distal and proximal half-sections 10a, 10b define a shell cavity 10c for receiving power-pack 101.

Figure 2:
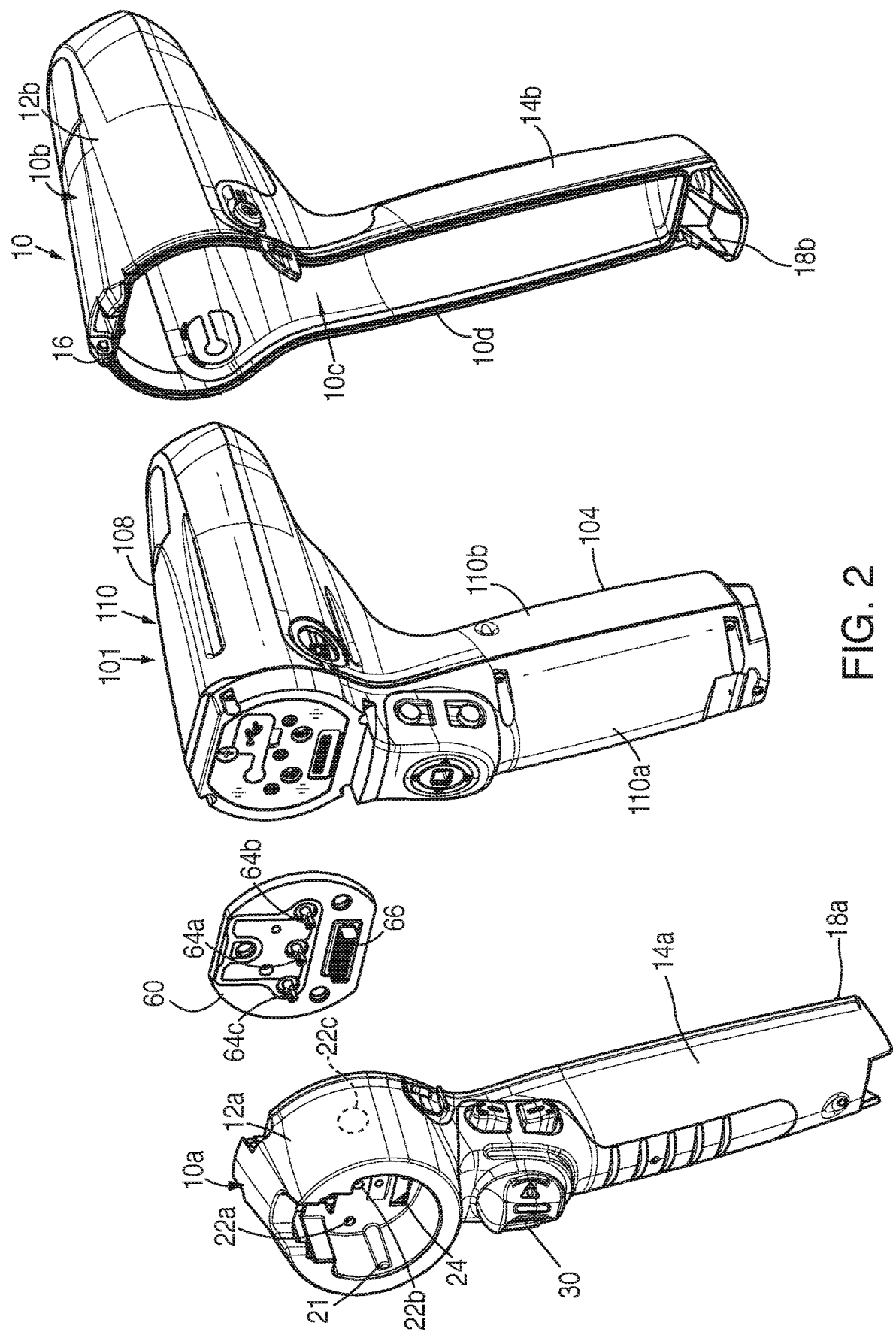
FIG. 2 is a front perspective view, with parts separated, of the handheld surgical device of FIG. 1.

With reference to FIG. 2, each of distal and proximal half-sections 10a, 10b includes a respective upper shell portion 12a, 12b, and a respective lower shell portion 14a, 14b. Lower shell portion 14a includes a closure tab 18a configured to engage a closure tab 18b of the lower shell portion 14b to selectively secure distal and proximal half-sections 10a, 10b to one another and for maintaining shell housing 10 in a closed configuration.

Distal half-section 10a of shell housing 10 also includes a connecting portion 20 configured to couple to a corresponding drive coupling assembly 210 of adapter 200. Specifically, the connecting portion 20 includes a recess 21 configured to receive a portion of drive coupling assembly 210 of adapter 200 when adapter 200 is mated to surgical device 100. Connecting portion 20 of distal half-section 10a also defines three apertures 22a, 22b, 22c and an elongate slot 24 formed in a distally facing surface thereof.

Distal half-section 10a of shell housing 10 also includes a plurality of buttons such as a toggle control button 30. In embodiments, toggle control button 30 may be a two-axis control stick configured to be actuated in a left, right, up and down direction. The toggle control button 30 may also be depressible.

Distal half-section 10a of shell housing 10 may also support a plurality of other buttons such as a right-side pair of control buttons and a left-side pair of control button.

These buttons and other components are described in detail in U.S. Patent Application Publication No. 2016/0310134, the entire disclosure of which is incorporated by reference herein.

With reference to FIG. 2, shell housing 10 includes a sterile barrier plate 60 removably supported in distal half-section 10a. The sterile barrier plate 60 interconnects the power-pack 101 and the adapter 200. Specifically, sterile barrier plate 60 is disposed behind connecting portion 20 of distal half-section 10a and within shell cavity 10c of shell housing 10. Plate 60 includes three coupling shafts 64a, 64b, 64c rotatably supported therein. Each coupling shaft 64a, 64b, 64c extends through a respective aperture 22a, 22b, 22c of connecting portion 20 of distal half-section 10a of shell housing 10.

Plate 60 further includes an electrical pass-through connector 66 supported thereon. Pass-through connector 66 extends through aperture 24 of connecting portion 20 of distal half-section 10a when sterile barrier plate 60 is disposed within shell cavity 10c of shell housing 10. Coupling shafts 64a, 64b, 64c and pass-through connector 66 electrically and mechanically interconnect respective corresponding features of adapter 200 and the power-pack 101.

During use, the shell housing 10 is opened (i.e., distal half-section 10a is separated from proximal half-section 10b about hinge 16), power-pack 101 is inserted into shell cavity 10c of shell housing 10, and distal half-section 10a is pivoted about hinge 16 to a closed configuration. In the closed configuration, closure tab 18a of lower shell portion 14a of distal half-section 10a engages closure tab 18b of lower shell portion 14b of proximal half-section 10b. Following a surgical procedure, shell housing 10 is opened and the power-pack 101 is removed from shell cavity 10c of shell housing 10. The shell housing 10 may be discarded and the power-pack 101 may then be disinfected and cleaned.

Figure 3:
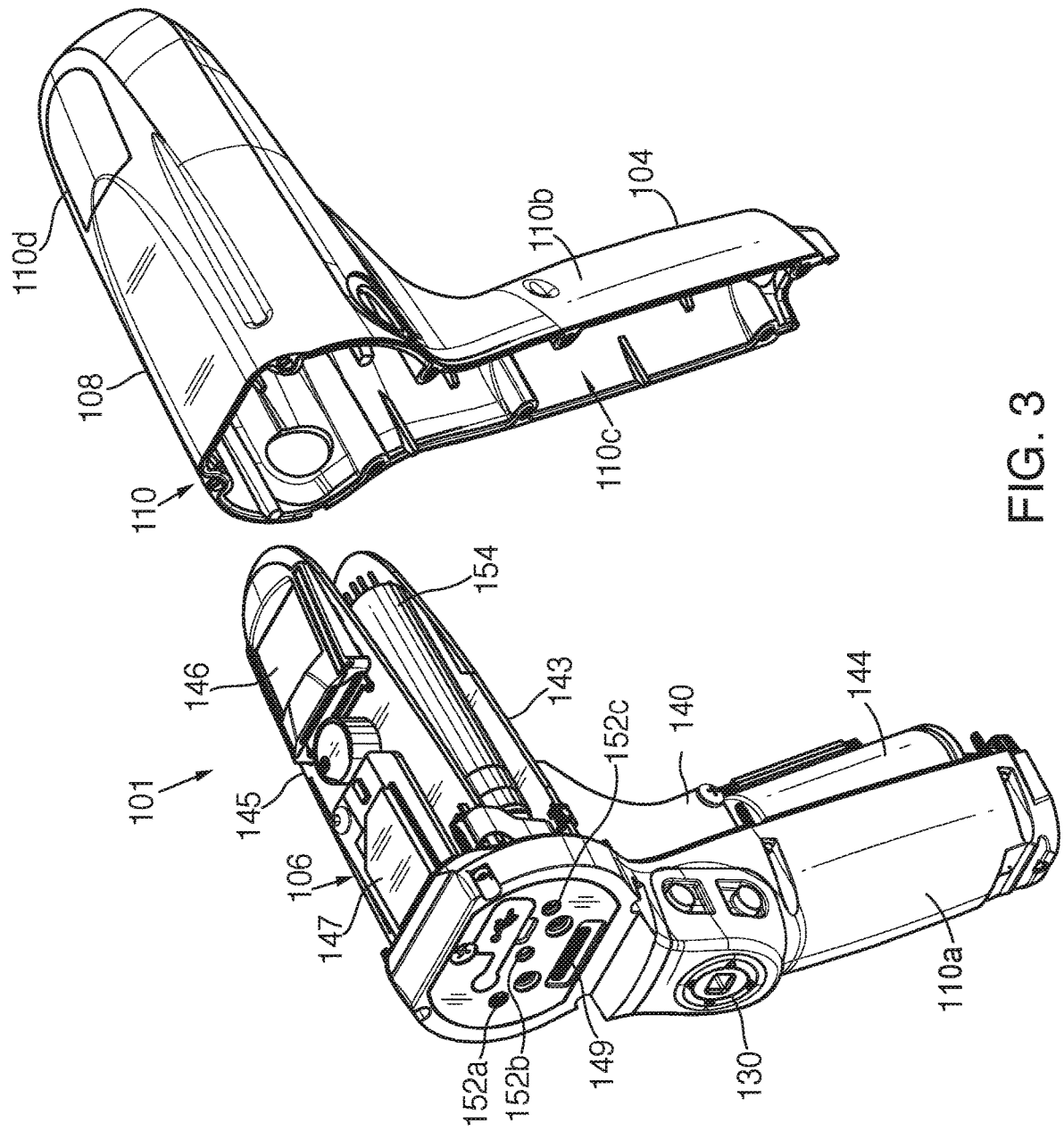
FIG. 3 is a front, perspective view of a power-pack and an inner rear housing of FIG. 2 separated therefrom.
Figure 4:
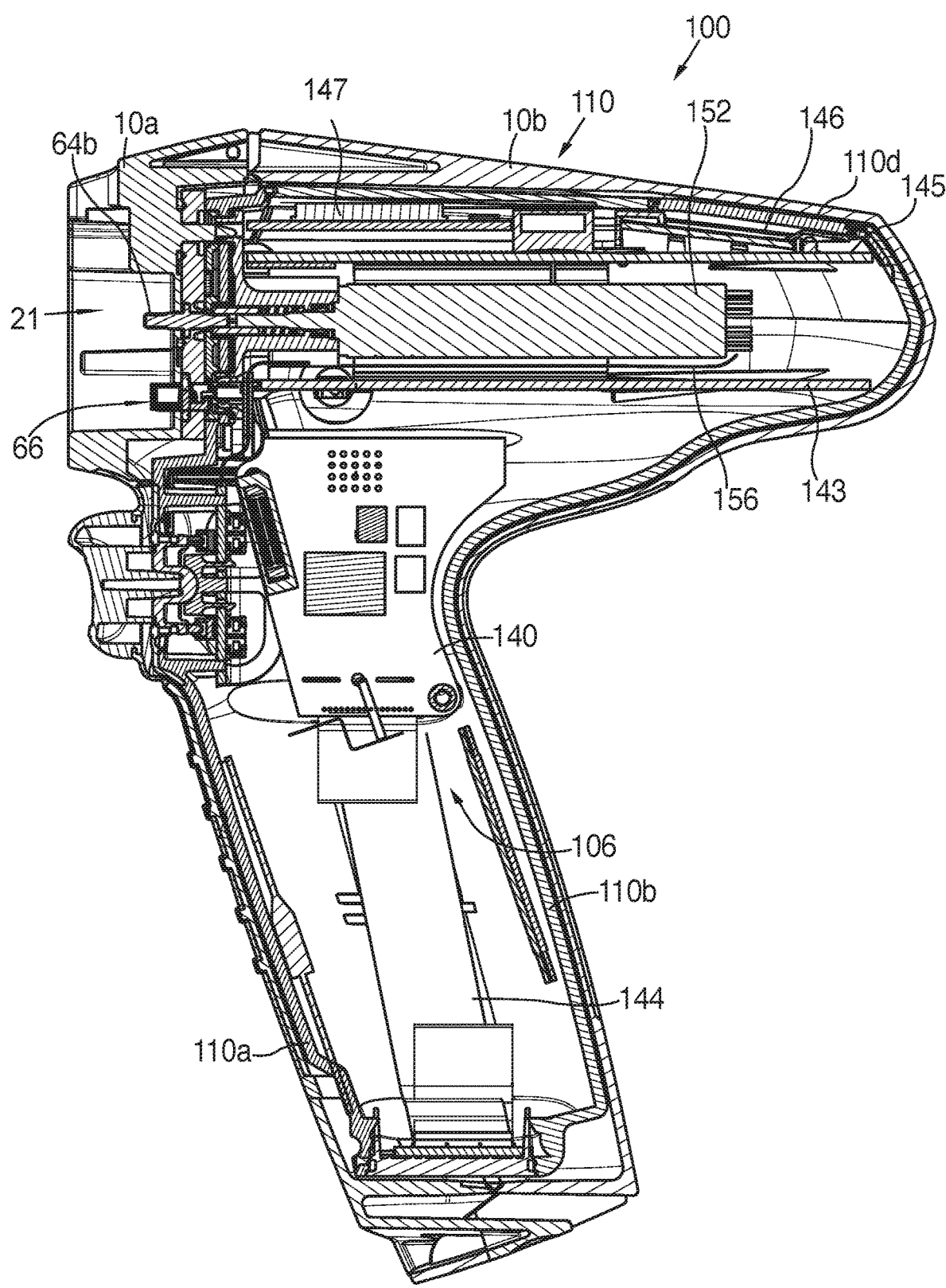
FIG. 4 is a cross-sectional view of the handheld surgical device of FIG. 2 taken along a section line "4-4"

Referring to FIGS. 2-4, power-pack 101 includes an inner handle housing 110 having a lower housing portion 104 and an upper housing portion 108 extending from and/or supported on lower housing portion 104. The inner handle housing 110 also includes a distal half-section 110a and a proximal half-section 110b, which define an inner housing cavity 110c (FIG. 3) for housing a power-pack core assembly 106 (FIG. 3). Power-pack core assembly 106 is configured to control the various operations of surgical device.

With reference to FIG. 3, distal half-section 110a of inner handle housing 110 supports a distal toggle control interface 130 that is operatively engaged with toggle control button 30 of shell housing 10, such that when power-pack 101 is disposed within shell housing 10, actuation of toggle control button 30 exerts a force on toggle control interface 130. Distal half-section 110a of inner handle housing 110 also supports various other control interfaces which operatively engage other buttons of shell housing 10.

With reference to FIGS. 3 and 4, power-pack core assembly 106 includes a battery circuit 140, a motor controller circuit 143, a main controller circuit 145, a main controller 147, and a rechargeable battery 144 configured to supply power to any of the electrical components of surgical device 100.

Power-pack core assembly 106 further includes a display screen 146 supported on main controller circuit 145. Display screen 146 is visible through a clear or transparent window 110d disposed in proximal half-section 110b of inner handle housing 110.

Power-pack core assembly 106 further includes a first motor 152 (FIG. 4), a second motor 154 (FIG. 3), and a third motor 156 (FIG. 4) each electrically connected to controller circuit 143 and battery 144. Motors 152, 154, 156 are disposed between motor controller circuit 143 and main controller circuit 145. Each motor 152, 154, 156 is controlled by a respective motor controller (not shown) that are disposed on motor controller circuit 143 and are coupled to a main controller 147. The main controller 147 is also coupled to memory 141 (FIG. 5), which is also disposed on the motor controller circuit 143. The main controller 147 communicates with the motor controllers through an FPGA, which provides control logic signals (e.g., coast, brake, etc. and any other suitable control signals). The motor controllers output corresponding energization signals to their respective motors 152, 154, 156 using fixed-frequency pulse width modulation (PWM).

Power-pack core assembly 106 also includes an electrical receptacle 149. Electrical receptacle 149 is in electrical connection with main controller board 145 via a second ribbon cable (not shown). Electrical receptacle 149 defines a plurality of electrical slots for receiving respective electrical contacts extending from pass-through connector 66 of plate 60 (FIG. 2) of shell housing 10.

Each motor 152, 154, 156 includes a respective motor shaft (not shown) extending therefrom. Each motor shaft may have a recess defined therein having a tri-lobe transverse cross-sectional profile for receiving proximal ends of respective coupling shaft 64a, 64b, 64c of plate 60 of shell housing 10.

Rotation of motor shafts by respective motors 152, 154, 156 actuates shafts and/or gear components of adapter 200 in order to perform the various operations of surgical device 100. In particular, motors 152, 154, 156 of power-pack core assembly 106 are configured to actuate shafts and/or gear components of adapter 200 in order to selectively actuate components of the end effector 400, to rotate end effector 400 about a longitudinal axis, and to pivot the end effector 400 about a pivot axis perpendicular to the longitudinal axis defined by the adapter 200.

Figure 5:
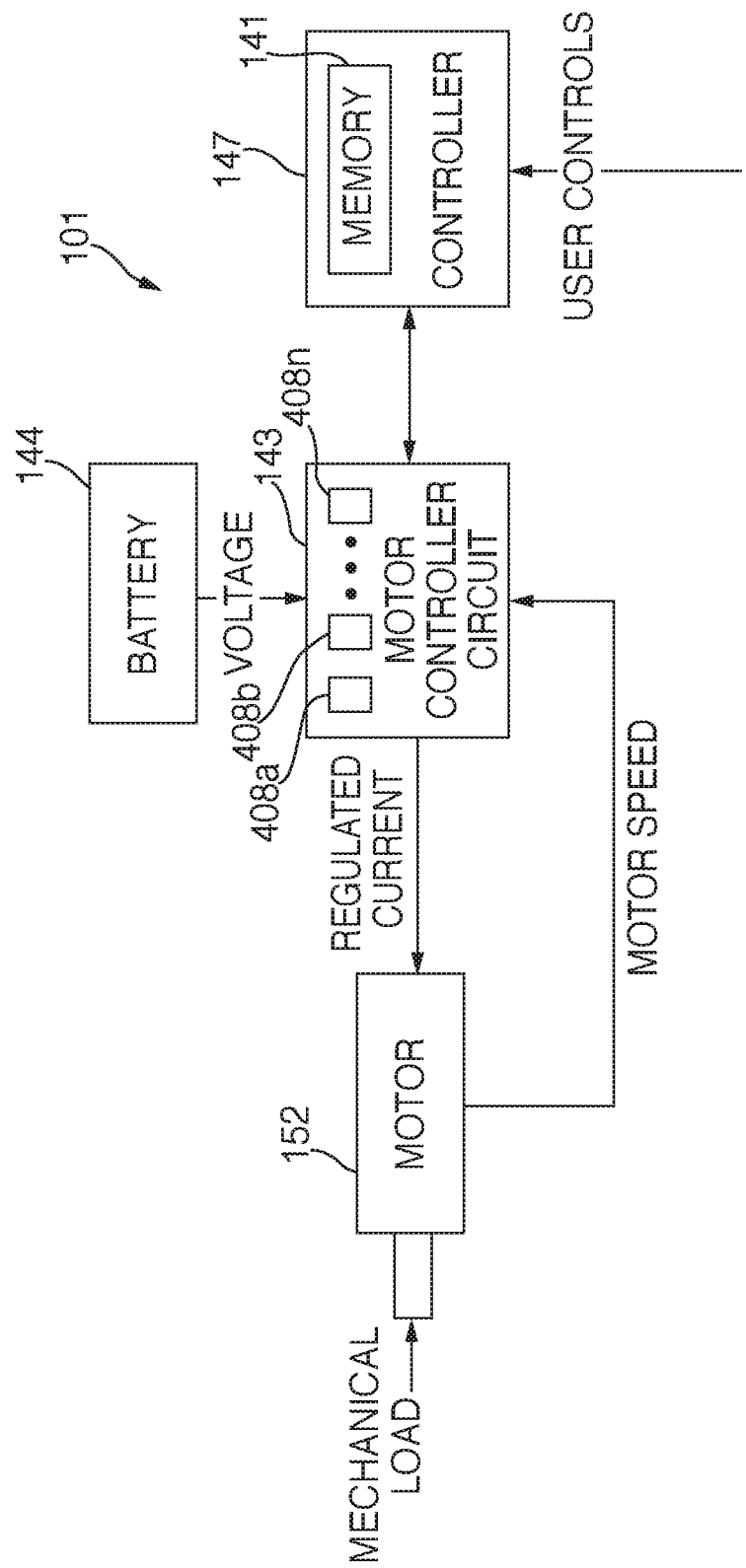
FIG. 5 is a schematic diagram of the handheld surgical device of FIG. 1 according to the present disclosure.

With reference to FIG. 5, a schematic diagram of the power-pack 101 is shown. For brevity, only one of the motors 152, 154, 156 is shown, namely, motor 152. The motor 152 is coupled to the battery 144. In embodiments, the motor 152 may be coupled to any suitable power source configured to provide electrical energy to the motor 152, such as an AC/DC transformer.

The battery 144 and the motor 152 are coupled to the motor controller circuit 143 which controls the operation of the motor 152 including the flow of electrical energy from the battery 144 to the motor 152. The motor controller circuit 143 includes a plurality of sensors 408a, 408b, . . . 408n configured to measure operational states of the motor 152 and the battery 144. The sensors 408a-n may include voltage sensors, current sensors, temperature sensors, telemetry sensors, optical sensors, and combinations thereof. The sensors 408a-408n may measure voltage, current, and other electrical properties of the electrical energy supplied by the battery 144. The sensors 408a-408n may also measure angular velocity (e.g., rotational speed) as revolutions per minute (RPM), torque, temperature, current draw, and other operational properties of the motor 152. Angular velocity may be determined by measuring the rotation of the motor 152 or a drive shaft (not shown) coupled thereto and rotatable by the motor 152. Position of various axially movable drive shafts may also be determined by using various linear sensors disposed in or in proximity to the shafts or extrapolated from the RPM measurements. In embodiments, torque may be calculated based on the regulated current draw of the motor 152 at a constant RPM. In further embodiments, the motor controller circuit 143 and/or the controller 147 may measure time and process the above-described values as a function thereof, including integration and/or differentiation, e.g., to determine the rate of change in the measured values.

The motor controller circuit 143 is also coupled to the controller 147, which includes a plurality of inputs and outputs for interfacing with the motor controller circuit 143. In particular, the controller 147 receives measured sensor signals from the motor controller circuit 143 regarding operational status of the motor 152 and the battery 144 and, in turn, outputs control signals to the motor controller circuit 143 to control the operation of the motor 152 based on the sensor readings and specific algorithm instructions, which are discussed in more detail below. The controller 147 is also configured to accept a plurality of user inputs from a user interface (e.g., switches, buttons, touch screen, etc. coupled to the controller 147).

The present disclosure provides for an apparatus and method for controlling the surgical device 100 or any other powered surgical instrument, including, but not limited to, linear powered staplers, circular or arcuate powered staplers, graspers, electrosurgical sealing forceps, rotary tissue morecellating devices, and the like. In particular, torque, RPM, position, and acceleration of drive shafts of the surgical device 100 can be correlated to motor characteristics (e.g., current draw). Current drawn by the motor 152 may be used for detecting mechanical limits since the current drawn by the motor 152 and its angular velocity change in response to the mechanical load encountered by the motor 152. Thus, analysis of the amount of change (e.g., rate of change) of current draw and angular velocity allows for distinguishing between different types of load conditions, e.g., load exerted by tissue versus load exerted by a mechanical stop.

Figure 6:
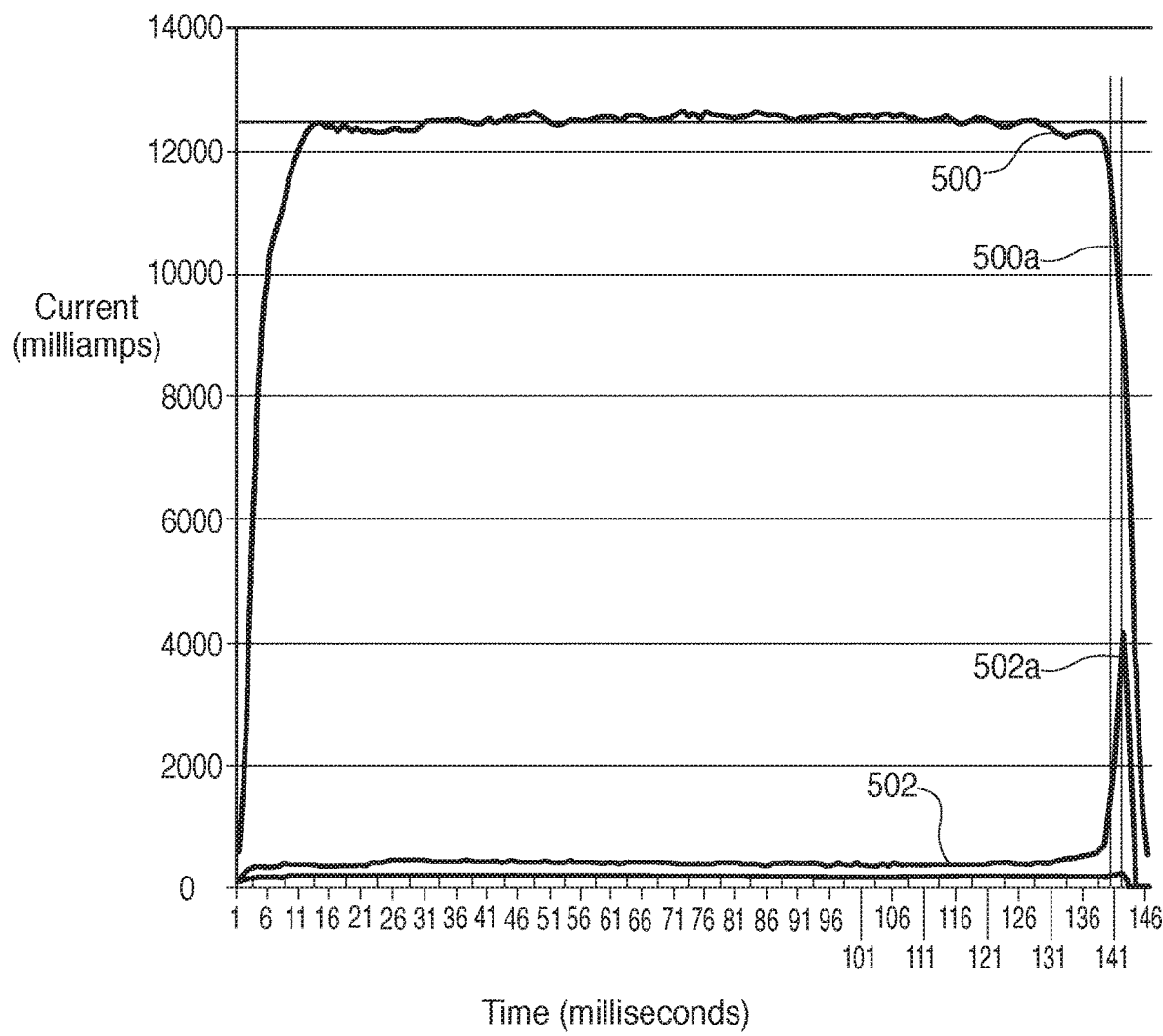
FIG. 6 is a plot of motor current and average angular motor velocity of the handheld surgical device of FIG. 1 as controlled by the method of the present disclosure.

The method according to the present disclosure for detecting mechanical limits may be used to detect collisions of mechanical components of the surgical system 2 (e.g., of end effector 400 and adapter 200), which may occur due to reaching end-of-travel positions or encountering obstructions by the end effector 400 during surgery. In further embodiments, intentional collisions may be used to calibrate motors 152, 154, 156 at start up or other times when the surgical device 100 needs to be recalibrated (e.g., attachment of a new adapter 200 or end effector 400). During calibration, the motor 152 is driven in a direction to cause a collision at a known mechanical position, e.g., a hard stop. Once the collision is detected by the controller 147, then the motor 152 is stopped, and the resulting angular motor position is designated as a zero position by the controller 147. In embodiments, collision may be detected by monitoring current draw of the motor 152 and detecting a current draw spike 502a of the plot 502 as shown in FIG. 6. With particular reference to FIG. 6, a current spike reaching approximately 4,000 milliamperes may be used to denote that the motor 152 has encountered its mechanical limit and a hardstop is detected.

With reference to FIG. 6, the current spike 502a begins to develop at approximately 1,390 milliseconds, whereas the spike 502a reaches its peak at approximately 1,430 milliseconds, resulting in a lag time of about 40 milliseconds, during which the motor 152 continues to actuate mechanical components. This excessive movement by the motor 152 may damage mechanical components and/or unnecessarily draw power from the battery 144. In addition, as the usable life efficiency of the motor 152 decreases, the motor 152 uses more current to perform the same amount of mechanical work. While a current filter or threshold that is used to determine the mechanical limit of about 4,000 milliamperes may be sufficient to determine that an actual collision has occurred when the motor 152 is relatively new, (e.g., less than 10 hours of operation) the same threshold may not be suitable for an older motor 152 (e.g., 20 hours of operation or more). In particular, a motor at the end of its usable life may cross the 4,000 threshold prior to actually encountering a mechanical limit, thus generating a false position for a hardstop by the controller 147. As a result of an incorrect identification of a zero position, the controller 147 may improperly calibrate the motor 152. In order to deal with this eventuality, current draw thresholds may be set high enough to prevent false collision protection over the life of the motor 152. However, this overcompensation results in motor stop current limits being higher than needed. As shown in FIG. 6, the current draw at about 40 milliseconds prior to collision is about ⅒ of the current draw threshold.

Figure 7:
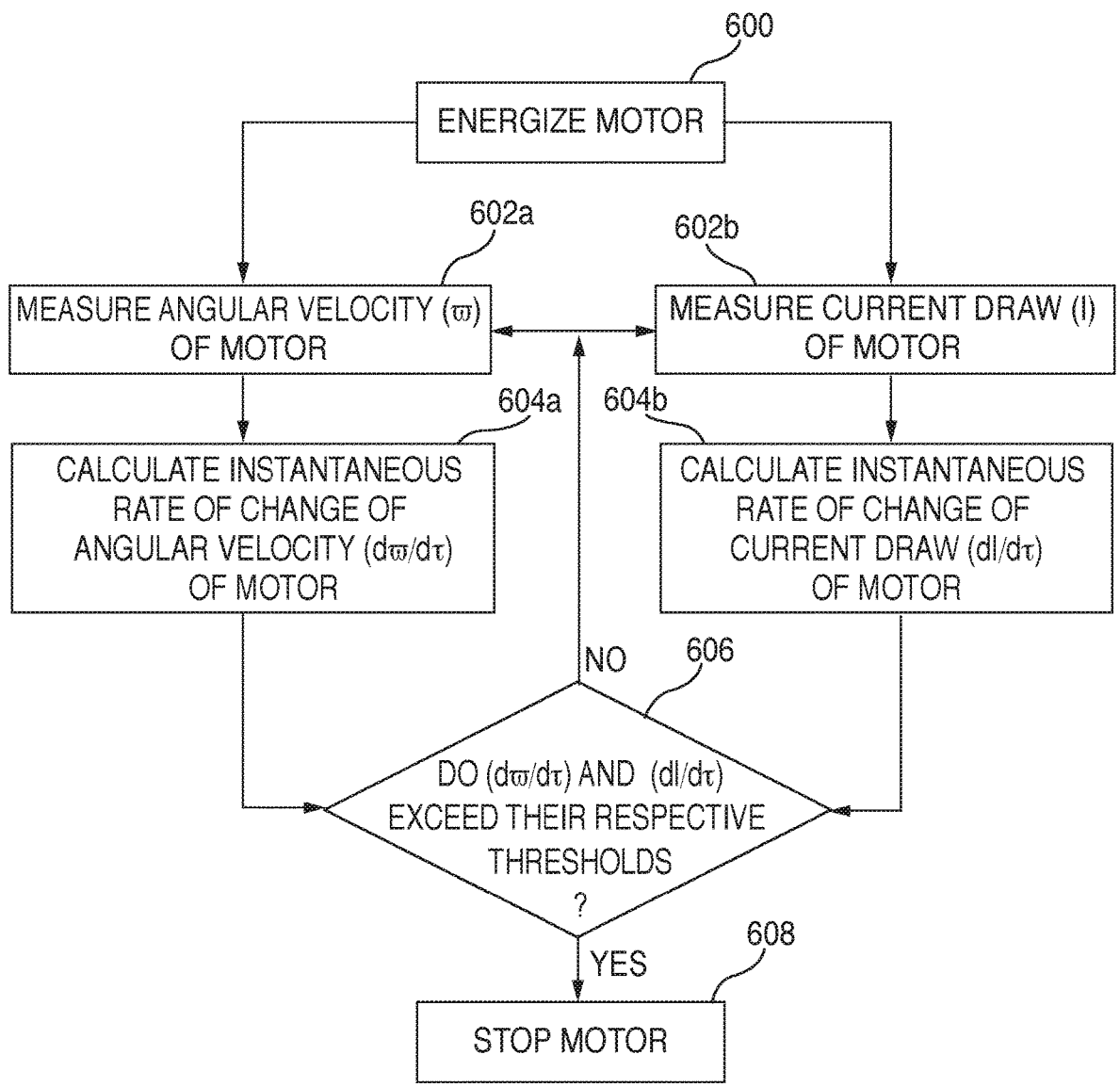
FIG. 7 is a flow chart of a method for controlling the handheld surgical device of FIG. 1 according to another embodiment of the present disclosure.

With reference to FIG. 7, a method according to the present disclosure for determining mechanical limits and/or collisions is disclosed. The method may be used to determine intentional collisions, such as during calibration, as well as unintentional collisions, such as during use of the surgical device 100. The method utilizes two values, namely, current draw and angular velocity, and rather than simply comparing the measured parameters to a predetermined threshold, the method calculates instantaneous rates of change of these parameters. The calculated instantaneous rates of change are then compared to respective rate of change thresholds. In embodiments, the method according to the present disclosure allows the surgical device 100 to detect the mechanical limits and/or collisions sooner than simply comparing measured motor parameters to thresholds.

The method may be embodied as an algorithm and computer-readable instructions executable by the controller 147. The controller 147 is coupled to the memory 141 or any other suitable, computer-readable, non-transitory medium for storing software instructions (e.g., algorithm) for detecting mechanical limits of the surgical device 100 based on the measured current draw and angular velocity. As used herein, the term "mechanical limit" denotes any of the electromechanical components reaching end-of-travel positions.

Initially, in step 600, the controller 147 signals the motor controller circuit 143 to operate the motor 152 based on desired user input, such as, for example, to control the motor 152, 154, 156 to articulate, actuate, or fire the end effector 400, or rotate the adapter 200 about its longitudinal axis. The controller 147 provides the desired command to the motor controller circuit 143, which then outputs corresponding energization signals to the motor 152 to effectuate the commands received from the controller 147. As the motor 152 is operated, the motor controller circuit 143 continuously monitors operational parameters of the motor 152 including angular velocity of the motor 152 as it is rotating and the current draw of the motor 152.

In steps 602a and 602b, the motor controller circuit 143 then measures and provides the angular velocity and current draw signals to the controller 147, respectively. In embodiments, the controller 147 may generate an angular velocity plot 500 and a current draw plot 502 as shown in FIG. 7 based on the received measurement data from the motor controller circuit 143. The plots 500 and 502 may be a collection of data points of the measurements collected by the motor controller circuit 143. In further embodiments, the plots 500 and 502 may not visualized or graphed by the controller 147 (e.g., output on a display device) and may be simply stored in the memory 141 for use by the controller 147.

In steps 604a and 604b, the controller 147 is configured to continuously process the measurement data of angular velocity and current draw, respectively, which includes continuously calculating the derivatives for each of these values. The controller 147 determines instantaneous rates of change for the angular velocity and the current draw. In embodiments, the controller 147 is configured to track the slopes of each of the plots 500 and 502, which are also calculated using the derivative function to obtain the instantaneous rates of change values.

In step 606, the controller 147 then compares the calculated instantaneous rates of change of each of the angular velocity and current draw of the motor 152 to their respective thresholds. With respect to angular velocity, the threshold corresponds to a negative slope or instantaneous rate of change since upon encountering a mechanical limit, the angular speed of the motor 152 decreases precipitously as shown by a spike 500a of plot 500 of FIG. 6. With respect to current draw, the threshold corresponds to a positive slope or instantaneous rate of change since upon encountering a mechanical limit, the current draw of the motor increases, as illustrated by a spike 502a of the plot 502 of FIG. 6. The angular velocity and current draw rates of change thresholds may be adjusted to eliminate false detection of mechanical limit detection.

The controller 147 determines that a mechanical limit is reached when both of the instantaneous rates of change of the angular velocity and the current draw exceed their respective predetermined thresholds concurrently. If this is so, the controller 147, confirms that a mechanical stop has been reached.

The controller 147 may then utilize the collision detection based on the use of the algorithm. During calibration, the controller 147 shuts down the motor 154 in step 608 and then assigns the position of the motor 152 to a zero position. The zero position is then used by the controller 147 to calculate longitudinal distance traveled by the mechanical components being actuated by the motor 152.

During use, the controller 147 may use the collision detection to signal the motor controller circuit 143 to stop the motor 152 in step 608, which then issues corresponding brake commands to the motor 152. In addition, the controller 147 may issue audio and/or visual alerts to the user that the surgical device 100 encountered an issue due to an unexpected collision and/or reaching a mechanical limit.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical instrument, comprising:
   a power source;
   a motor coupled to the power source, the motor configured to actuate at least one component of a surgical instrument; and
   a controller operatively coupled to the motor and configured to:
      calculate an instantaneous rate of change of a current draw of the motor;
      calculate an instantaneous rate of change of an angular velocity of the motor; and
      determine that the motor reached a mechanical limit based on the instantaneous rate of change of the current draw of the motor exceeding a first threshold and the instantaneous rate of change of the angular velocity of the motor exceeding a second threshold.

2. The surgical instrument according to claim 1, wherein the controller is configured to determine that the motor reached a mechanical limit based on the instantaneous rate of change of the current draw of the motor being positive and the instantaneous rate of change of the angular velocity of the motor being negative.

3. The surgical instrument according to claim 1, wherein the controller is configured to determine that the motor reached the mechanical limit based on the instantaneous rate of change of the current draw of the motor exceeding the first threshold concurrently with the instantaneous rate of change of the angular velocity of the motor exceeding the second threshold.

4. The surgical instrument according to claim 3, wherein the controller is configured to calibrate the motor based on the mechanical limit.

5. The surgical instrument according to claim 1, wherein the controller is configured to terminate a supply of electrical current to the motor from the power source in response to detection of the mechanical limit.

6. A method for controlling a surgical device, the method comprising:
   energizing a motor to actuate at least one component of a surgical device;
   calculating an instantaneous rate of change of a current draw of the motor;
   calculating an instantaneous rate of change of an angular velocity of the motor; and
   determining that the motor reached a mechanical limit based on the instantaneous rate of change of the current draw of the motor exceeding a first threshold and the instantaneous rate of change of the angular velocity of the motor exceeding a second threshold.

7. The method according to claim 6, further comprising:
   determining that the motor reached a mechanical limit based on the instantaneous rate of change of the current draw of the motor being positive and the instantaneous rate of change of the angular velocity of the motor being negative.

8. The method according to claim 6, further comprising:
   determining that the motor reached the mechanical limit based on the instantaneous rate of change of the current draw of the motor exceeding the first threshold concurrently with the instantaneous rate of change of the angular velocity of the motor exceeding the second threshold.

9. The method according to claim 8, further comprising:
   calibrating the motor based on the mechanical limit.

10. The method according to claim 6, further comprising:
    terminating a supply of electrical current to the motor from a power source in response to detection of the mechanical limit.

11. A method for calibrating a surgical instrument, the method comprising:
    energizing a motor to actuate at least one component of a surgical instrument;
    measuring a current draw of the motor;
    measuring an angular velocity of the motor;

detecting the motor reaching a mechanical limit based on the current draw of the motor and the angular velocity of the motor; and designating an angular position of the motor corresponding to the mechanical limit as a zero position for calibrating the motor.

12. The method according to claim 11, further comprising:

calculating an instantaneous rate of change of each of the current draw of the motor and the angular velocity of the motor.

13. The method according to claim 12, further comprising:

determining that the motor reached the mechanical limit based on the instantaneous rate of change of the current draw of the motor being positive and the instantaneous rate of change of the angular velocity of the motor being negative.

14. The method according to claim 13, further comprising:

determining that the motor reached the mechanical limit based on the instantaneous rate of change of the current draw of the motor exceeding a first threshold and the instantaneous rate of change of the angular velocity of the motor exceeding a second threshold.

15. The method according to claim 13, further comprising:

determining that the motor reached the mechanical limit based on the instantaneous rate of change of the current draw of the motor exceeding a first threshold concurrently with the instantaneous rate of change of the angular velocity of the motor exceeding a second threshold.

* * * * *